United States Patent
Popilka et al.

(10) Patent No.: US 9,462,993 B2
(45) Date of Patent: Oct. 11, 2016

(54) METHOD AND REFERENCE MODEL FOR CHECKING A MEASURING SYSTEM

(71) Applicants: Björn Popilka, Hemsbach (DE); Volker Wedler, Hirschberg (DE); Anders Adamson, Darmstadt (DE); Frank Thiel, Ober-Ramstadt (DE)

(72) Inventors: Björn Popilka, Hemsbach (DE); Volker Wedler, Hirschberg (DE); Anders Adamson, Darmstadt (DE); Frank Thiel, Ober-Ramstadt (DE)

(73) Assignee: Sirona Dental Systems GmbH, Bensheim (DE)

( * ) Notice: Subject to any disclaimer, the term of this patent is extended or adjusted under 35 U.S.C. 154(b) by 61 days.

(21) Appl. No.: 14/372,255

(22) PCT Filed: Jan. 28, 2013

(86) PCT No.: PCT/EP2013/051547
§ 371 (c)(1),
(2) Date: Jul. 15, 2014

(87) PCT Pub. No.: WO2013/110806
PCT Pub. Date: Aug. 1, 2013

(65) Prior Publication Data
US 2014/0365140 A1 Dec. 11, 2014

(30) Foreign Application Priority Data
Jan. 27, 2012 (DE) .................... 10 2012 201 193

(51) Int. Cl.
*A61B 6/00* (2006.01)
*A61B 5/107* (2006.01)
(Continued)

(52) U.S. Cl.
CPC ............ *A61B 6/582* (2013.01); *A61B 5/1077* (2013.01); *A61B 5/1079* (2013.01); *A61C 19/04* (2013.01);
(Continued)

(58) Field of Classification Search
None
See application file for complete search history.

(56) References Cited

U.S. PATENT DOCUMENTS 4,073,071 A * 2/1978 Angelotti ............. G09B 23/283
434/185
6,078,701 A * 6/2000 Hsu .......................... G06K 9/32
375/E7.086

(Continued)

FOREIGN PATENT DOCUMENTS

DE       89 15 044 U1      6/1990
EP       0 895 192 A1      2/1999
(Continued)

OTHER PUBLICATIONS

Jaeggli, Tobias, Thomas P. Koninckx, and Luc Van Gool. "Online 3d acquisition and model integration." Proc. IEEE Int'l Workshop Projector-Camera Systems. 2003.*
(Continued)

*Primary Examiner* — Chan Parl
*Assistant Examiner* — Geoffrey E Summers
(74) *Attorney, Agent, or Firm* — Fitzpatrick, Cella, Harper & Scinto

(57) ABSTRACT

The invention relates to a reference object (3) and a method for checking a measuring system (1), wherein a plurality of three-dimensional recordings (4, 8) of a reference object are recorded from different recording directions (5) by means of the measuring system (1). The reference object (3) has a closed shape, wherein each of the three-dimensional recordings (4) is registered with at least the preceding recording (4). In the case of a faulty calibration and/or in the case of a faulty registration, the individual recordings (4, 8) are deformed compared to the actual shape of the reference object (3), so that the deformation continues when assembling the individual three-dimensional recordings (4) to form an overall recording (54) and the generated overall recording (54) deviates in its dimensions from the dimensions of the reference object (3) as a result thereof. At least one object region (10) of the reference object (3) is measured twice, at the beginning of a circuit and at the end of the circuit, wherein a distance (55) is determined in the overall recording (54) between a first position of the object region (10) in a first recording at the beginning of the circuit and a second position of the object region (10) in a second recording at the end of the circuit.

14 Claims, 3 Drawing Sheets

(51) Int. Cl.
G06T 7/00 (2006.01)
G01B 21/04 (2006.01)
A61C 19/04 (2006.01)
G06T 19/20 (2011.01)
G09B 23/28 (2006.01)
A61C 9/00 (2006.01)
A61C 13/34 (2006.01)

(52) U.S. Cl.
CPC ............ G01B 21/042 (2013.01); G06T 7/002 (2013.01); G06T 7/0018 (2013.01); G06T 19/20 (2013.01); *A61B 2560/0233* (2013.01); *A61C 9/006* (2013.01); *A61C 9/0066* (2013.01); *A61C 13/34* (2013.01); *G06T 2207/30036* (2013.01); *G06T 2207/30204* (2013.01); *G06T 2219/2004* (2013.01); *G09B 23/283* (2013.01)

(56) References Cited

U.S. PATENT DOCUMENTS 8,711,206 B2 * 4/2014 Newcombe ............... G06T 7/20 348/142

2007/0171220 A1 * 7/2007 Kriveshko ......... A61C 13/0004 345/419
2013/0329020 A1 * 12/2013 Kriveshko ......... A61B 1/00009 348/50

FOREIGN PATENT DOCUMENTS

WO 2010/077380 A2 7/2010
WO 2011/106472 A1 9/2011

OTHER PUBLICATIONS

DeLong, R., et al. "Accuracy of a system for creating 3D computer models of dental arches." Journal of dental research 82.6 (2003): 438-442.*

Brusco, Nicola, et al. "Metrological validation for 3D modeling of dental plaster casts." Medical engineering & physics 29.9 (2007): 954-966.*

T. Jaeggli et al., "Online 3D Acquisition and Model Integration," in Proc. IEEE International Workshop on Projector-Camera Systems (2003) 1-8.

* cited by examiner

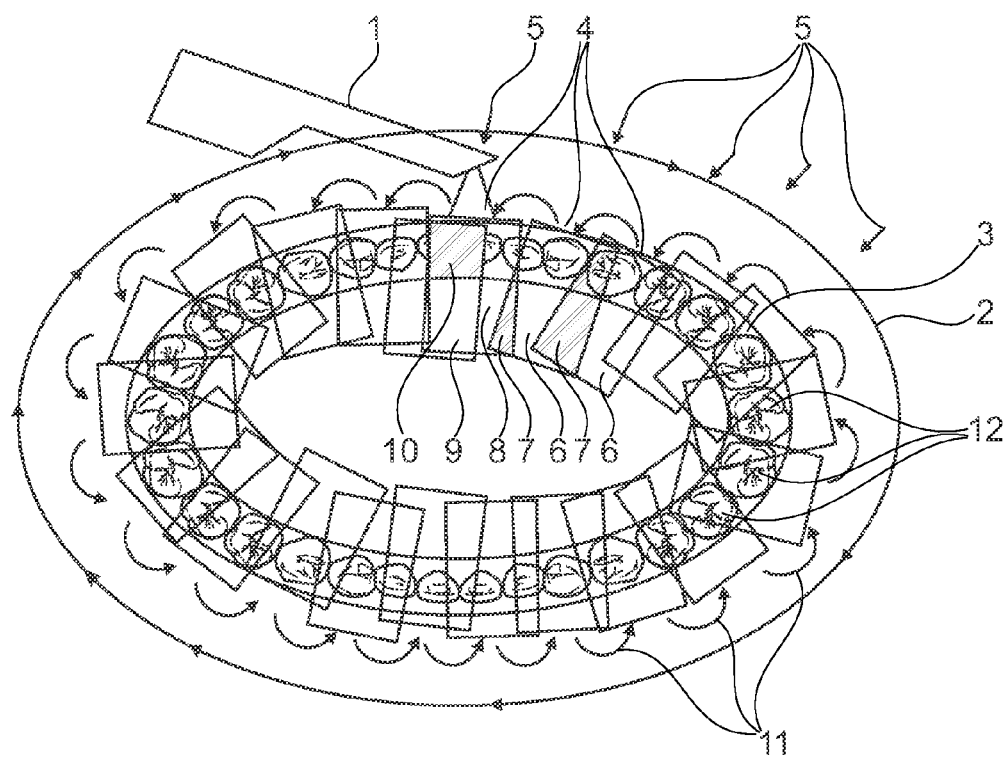
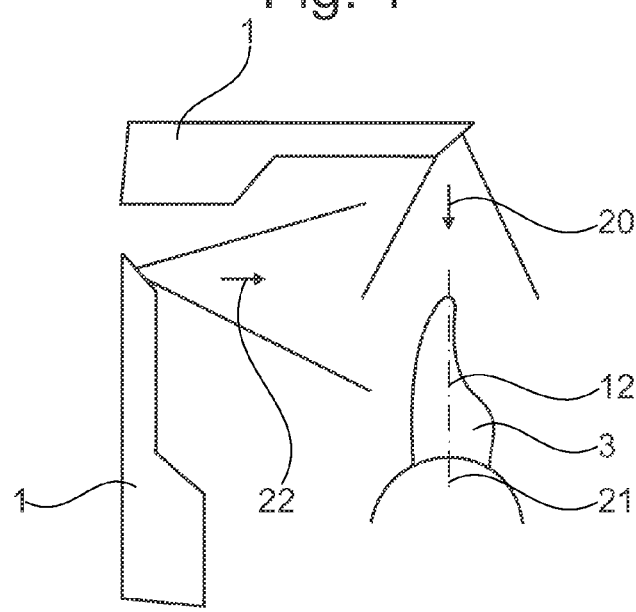
Fig. 1
Fig. 2

METHOD AND REFERENCE MODEL FOR CHECKING A MEASURING SYSTEM

CROSS REFERENCE TO RELATED APPLICATIONS

The present application is a national-stage entry under 35 U.S.C. 371 of International Application No. PCT/EP2013/051547 filed Jan. 28, 2013, and claims the benefit of foreign priority under 35 U.S.C. 119 of German Application No. 10 2012 201 193.5 filed Jan. 27, 2012. Each of those applications is hereby incorporated by reference as if set forth fully herein.

TECHNICAL FIELD

The invention relates to a method for checking a measuring system, wherein a plurality of three-dimensional images of a reference object are recorded from different image directions by means of the measuring system.

PRIOR ART

A plurality of methods for checking a measuring system are known from the prior art.

In a first method, a reference model is measured by means of a precise laboratory system in a first step, and a 3-D model of the reference model is generated in doing so. Then, in a second step, the same reference model is measured by means of the measuring system to be checked, and a second 3-D model is generated. Subsequently, the first 3-D model measured with the laboratory system is compared with the second 3-D model. The difference between the two 3-D models then indicates a faulty calibration or registration. The difference between the 3-D models can be shown, for example, with false color markings. An average value of the deviation can also be depicted by determining the difference for multiple measuring points along a normal vector for the entire surface of the 3-D model.

With an alternative second method, a reference model with known dimensions can be measured by means of the measuring system to be checked in which a 3-D model is generated. This difference model may be, for example, a model of a maxilla or a mandible. After the measurement, the distance, for example, between the occlusal surfaces of the last teeth of the maxilla or of the mandible is measured in the 3-D model and compared with the actual distance between the two last teeth of the reference model. A deviation between the two distances indicates a registration error and/or a calibration error.

A disadvantage of this method is that the dimensions of the reference model, just as the distance between the last teeth of the maxilla or the mandible, must either be precisely measured or already known in order to enable a comparison. Marking with false colors and the determination of an average value of the deviation requires extensive technical effort and makes it difficult for the user to determine whether the accuracy of the calibration and/or the registration is within the permissible tolerance limits or not.

The object of the present invention is thus to provide a method and a reference model to check a measuring system that will enable simple checking of a measuring system without extensive technical effort.

DESCRIPTION OF THE INVENTION

The invention relates to a method for checking a measuring system, wherein a plurality of three-dimensional images of a reference object are recorded from different image directions by means of the measuring system. The reference object in this case has a closed shape. Each of these three-dimensional images is registered at least with the preceding image, during which, with a faulty calibration and/or with a faulty registration, the individual images are deformed in comparison to the actual shape of the reference object, which means that the deformation continues when combining the individual three-dimensional images to form an overall image, and the overall image generated deviates in its dimensions from the dimensions of the reference object as a result thereof. In this process, at least one object region of the reference object is measured twice, at the beginning of a circuit and at the end of the circuit. A distance is then determined in the overall image between a first position of the object region in a first image at the beginning of the circuit, and a second position of the object region in a second image at the end of the circuit.

Advantageously, a measuring error in the measuring system, which comprises a calibration error and/or a registration error, can then be determined using this distance.

The measuring system for three-dimensional optical measurement may be based, for example, on a fringe projection method, a confocal optical method, or on a colored fringe projection method. The measuring system to be checked may also be based on an x-ray computer tomography method (CT). With an optical three-dimensional measuring system, a plurality of three-dimensional optical images of a reference object is generated from different image directions, and the individual images are then combined to form an overall image. With a CT measuring system, multiple x-ray projected images comprising multiple image devices are taken of the reference object. The individual x-ray projected images are then combined into one three-dimensional x-ray image of the reference object while using computer-supported image reconstruction.

An image is triggered by the user while, in the second step, the dental camera is moved further relative to the reference object, and subsequently a second image is triggered. In this manner, multiple images are taken from different image directions until the reference object has been completely recorded. This means that the image regions of the images have different distances with respect to one another, which may vary.

The measurement may also be done while using a turntable, during which the reference object is rotated around a certain section of angle for each image. In this manner, the measurement can be repeated under the same conditions. The image regions of the individual images have defined overlapping regions due to the specified image directions, which means that the results of the registration are reproducible. The turntable can be actuated accordingly by means of an actuation device and synchronized with the measuring system. This enables automated measuring under defined conditions.

The closed shape of the reference object may be, for example, circular, oval, or the shape of any three-dimensional loop. For example, the closed shape may correspond to the outline of a conventional articulator with a maxilla, a mandible, and the connecting points between the maxilla and mandible. During the registration, each of the images is registered with the previous image. In addition, each of the images can be registered with the image before last, which is arranged before the previous image. This further improves the results of the registration. However, the requirement for this additional registration is that the three images have overlapping regions in common.

The registration is done in the conventional manner using known registration algorithms during which matching structures are detected in the images and combined. If the algorithms are faulty, the registration may be faulty and cause registration errors. The presence of such a registration error can be detected by means of the present method. A registration error may also be caused by noisy images or by an image with a very low resolution.

The registration takes place image-by-image along the entire closed shape of the reference object up to the starting point of registration. If the registration is faulty, a first position of the first image region will deviate from the position of the same image region over the course of registration of the entire reference object. For the user, it is immediately clearly discernible that the measuring system has a measuring error.

The measurement of the reference object and the subsequent registration can also take place in more than one circuit along the closed shape. The image region to be compared on the actual reference object can be selected as desired. A specific characteristic point on the reference object may also be used for the comparison. This selected image region or the characteristic point is then determined with the use of known registration algorithms at the start of a circuit and at the end of the circuit along the closed shape, which means that a distance between the image region to be compared or the characteristic point can be determined. This distance indicates the extent of the measuring error of the measuring system.

The measuring error can also be caused by a calibration error, in addition to the registration error. The calibration error may be caused, for example, by faulty settings in the camera parameters of the measuring system. With a measuring system based on the fringe projection method, the definitive camera parameters are the distance between the camera and the reference object, the angle of incidence, as well as a lattice spacing of a lattice for generating a stripe pattern.

The camera parameters may also be based on a pinhole camera model in which a differentiation is made between intrinsic and extrinsic. Potential intrinsic parameters are, for example, the focal length of the camera, the pixel coordinates of the center of the image, and the distortion parameters. The extrinsic parameters may comprise the rotation and the translation between the camera and the projector.

The individual images may also be taken at short intervals, one after another, for example at more than 10 Hz. This enables a so-called over-flight measurement in which the handheld dental camera is moved evenly over the reference object to be measured, and its images are simultaneously taken from different image directions with image regions that have sufficiently large overlapping regions for the registration.

The reference object has three-dimensional objects that are suitable for clear registration.

These objects may be in any geometric shapes such as cubes, tetrahedrons, or semi-circles which are distributed in an unordered manner. The objects may also be models of teeth that are arranged next to one another in a row.

An advantage of this method is that the dimensions of the reference object do not have to be known in order to check the measuring system. The measuring error is solely determined by comparing an image region at the start of a circuit and at the end of a circuit in the overall image generated. In comparison to methods in which the images of the measuring system are compared to sample images of a calibrated laboratory system, the difference is that, with the present method, a potential measuring error from such a laboratory system is excluded.

Advantageously, the reference object may be in the shape of a ring and have models of multiple teeth arranged next to one another in a row.

This imitates the realistic measuring conditions of the measuring system, namely the measuring of teeth of a maxilla or a mandible. The ring-shaped arrangement of the teeth may comprise, for example, all the teeth of a maxilla or a mandible in the correct sequence. This means that the two last molars are adjacent one another.

Advantageously, a trajectory of the measuring system can extend in a circle around the ring-shaped reference object while the images are being recorded from the different image directions.

This means that multiple images are taken from image directions with certain angular distances with respect to one another so that the overlapping regions of the image regions are sufficient for the registration.

Advantageously, the reference object may correspond to a conventional articulator with a maxilla and a mandible having a closed shape.

This means that a conventional articulator may be used as the reference object which has a maxilla, a mandible, and connecting rods between the maxilla and the mandible. The measuring system is then guided along the course of this articulator in which multiple images are created until the entire articulator is recorded.

Advantageously, a trajectory of the measuring system can extend along the shape of the articulator while the images are being recorded from the different image directions.

This means that the entire articulator is completely recorded such that registration can be carried out.

Advantageously, the image direction of a last image in the sequence of images can correspond with the image direction of a first image.

Hence merely one circuit is required for completing the method. The first image and the last image are then utilized for the comparison, during which the image region to be compared is detected while using the pattern detection method in the first image and in the last image, and a distance is determined between the first position of the image region or of the characteristic point in the first image, and the image region or of the characteristic point in the last image.

Advantageously, a first image region of the reference object of a first image in the sequence of the images can correspond, at least partially, with an image region of the following images.

This means that the measurement will take place in more than one circuit so that some image regions will be measured twice. These image regions measured at the start of a circuit and at the end of the circuit can be used for the comparison.

Advantageously, the registration error can be determined before completion of the three-dimensional images by cutting out virtual individual sub-regions, one after another, from a first original virtual 3-D model, in which each sub-region partially overlaps with a previous sub-region and with a following sub-region. Subsequently, each sub-region is registered with at least one previous sub-region such that a second virtual 3-D model of the reference object is generated after the registration. The registration error is then determined from a deviation between the first original 3-D model and the second 3-D model of the reference object.

This means that the registration error is determined before the measurement in that sub-regions are virtually cut out of the ideal first 3-D model and registered. The calibration error can also be determined subsequently by subtracting the registration error from the measuring error.

Advantageously, the dimensions of the sub-regions, which are cut out of the first original 3-D model, correspond to the image regions of the individual images to be taken.

This enables the registration to be simulated as precisely as possible during the measurement. If the overlapping regions deviate, the registration can lead to a different result.

Advantageously, the calibration error can be determined by subtracting the registration error from the total measuring error.

This makes it clear whether the measuring error is caused more by the faulty registration or by the faulty calibration.

Advantageously, each image can partially overlap with the preceding image and with the image before that, wherein each image is registered with the preceding image and with the image before that.

This will additionally improve the registration. A requirement for this is for the image regions be close enough to one another so that each image has overlapping regions with the preceding image and with the image before that. Registration can also be done with the image before the image before the preceding image if it has matching transition regions.

The invention further relates to a reference model for checking a dental measuring system for measuring three-dimensional images. The reference model is constructed from multiple models of teeth and has a closed shape.

This reference model is suitable for carrying out the aforementioned method. Contrary to conventional reference models that correspond to the dimensions of a maxilla or a mandible, the present reference model has a closed shape. This has the advantage that when measuring the reference model, the measuring system once again reaches the starting point after a circuit, which means that a first image at the start of a circuit can be easily compared with a second image at the end of a circuit in order to determine measuring errors.

Advantageously, the reference model may be in the shape of a ring.

This means that the measurement will proceed along a circular trajectory. Such a measurement may be implemented by means of an automated turntable upon which the reference object is placed.

Advantageously, the models may correspond to multiple teeth of a maxilla and/or a mandible.

This means that the dental measuring system may be checked under realistic measuring conditions.

The present method for checking measuring systems is particularly suitable for quality control when producing such measuring systems at the manufacturer's. The present method may also be used, however, for a recheck of such measuring systems at consumers, for example in a dental practice. To this end, the user only requires the aforementioned reference object which is measured by means of the measuring system. To implement the method, the user may also require additional software that determines the deviation and the measuring error. This means that any measuring system may be retrofitted in a simple manner in order to conduct the present method.

BRIEF DESCRIPTION OF THE DRAWINGS

The invention will be explained with reference to the drawings. In the following:

FIG. 1 shows a drawing to clarify the present method;
FIG. 2 shows a side view of the reference object comprising an incisor.

EXEMPLARY EMBODIMENT

Figure 3:
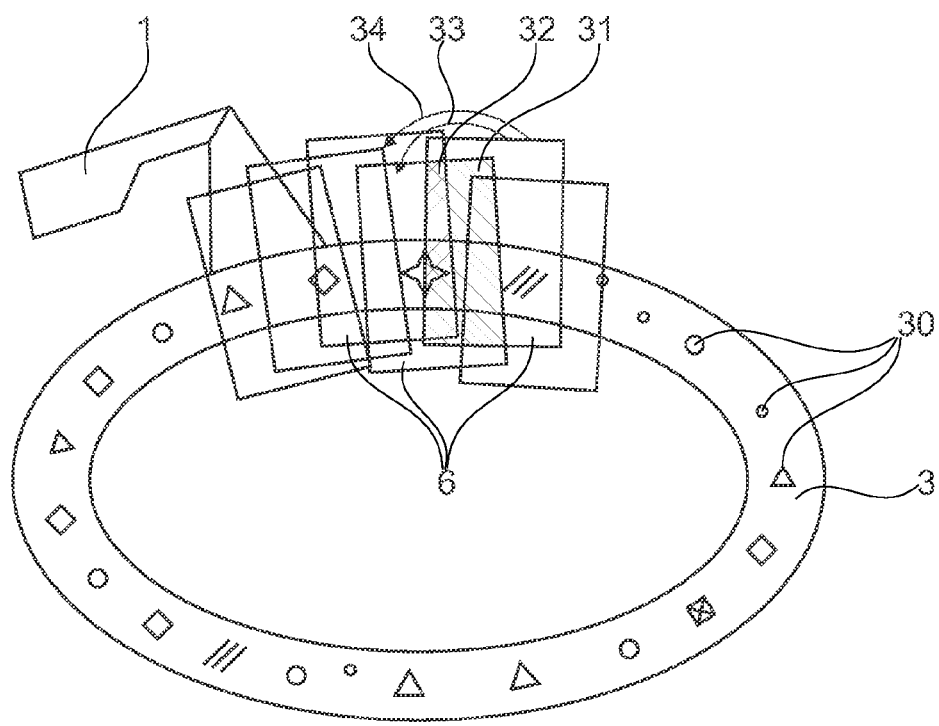
FIG. 3 shows an alternative reference object.

FIG. 1 shows a drawing to clarify the present method for checking a measuring system 1, such as a dental camera. The dental camera 1 can function according to any three-dimensional measuring system, for example according to a fringe projection method or a confocal measuring system. To implement the method, the measuring system 1 is moved along a trajectory 2 around a reference object 3, during which multiple three-dimensional images 4 are taken from different image directions 5 which are indicated by arrows. The measuring system 1 proceeds at least once around the reference object 3 along the trajectory 2. The image regions 6 of the images 4 are rectangular in this case and have overlapping regions 7 with respect to the particular preceding image region, and are depicted with hatching. A first image is initially taken with a first image region 8 and, after one circuit, a final image of this circuit is taken with a second image region 9, in which an object region 10 of the reference object 3 to be compared, which is represented with hatching, is contained both in the first image 8 of the circuit and in the last image 9 of the circuit. Each of the images 4 is registered at least with the preceding image, as indicated by the arrows 11. If the image regions 6 are close enough to one another, each image can additionally be registered with the preceding image and the image before that for registration. The registration thus continues image-by-image until all individual images 4 are combined into one overall image of the entire reference object. If the registration and/or the calibration of the measuring system are faulty, each of the three-dimensional images 4 will be slightly deformed in comparison to the actual dimensions of the reference object 3, which means that this deformation will continue when the individual images 4 are combined. Using this deviation between the overall image and the actual dimensions of the reference object 3, the measuring error is then determined which comprises a calibration error and/or a registration error. In the present case, the reference object is shaped like a ring and formed from multiple models of teeth 12 next to one another in a row, wherein the upper half of the reference model comprises the teeth of a maxilla, and the lower half of the reference model comprises teeth of a mandible. The reference model may also comprise other three-dimensional models suitable for registration. It is essential in this case that the three-dimensional models not form any repeating patterns and that they be uniquely identifiable. The measurement may also go beyond one circuit, which means that multiple object regions of the reference object 3 are measured twice. In such a case, one of these object regions can be used for the comparison and determination of the measuring error. The advantage of this method is that the actual dimensions of the reference object do not have to be known to determine the measuring error.

FIG. 2 shows a side view of the reference object 3 comprising an incisor 12. The measurement by means of the dental camera 1 takes place, in a first step, from a first image direction 20, which proceeds somewhat parallel to a tooth axis 21 of the tooth 12 and subsequently, in a second step, the reference object 3 is measured from a second image direction 22. This means that the three-dimensional shape of the reference object 3 is recorded both from above, from the first image direction 20, as well as from the side, from the second image direction 22. In this manner, the entire reference object 3 is measured tooth-by-tooth along a circuit. The advantage of the additional side measurement is that the registration is improved by a larger surface of the reference object 3 to be registered.

In comparison to FIG. 1, FIG. 3 shows an alternative reference object 3 that has three-dimensional models in the shape of geometric basic shapes, such as hemispheres, tetrahedrons, or pyramids, instead of teeth. Contrary to FIG. 1, the image regions 6 are so close to one another that each image region has a first overlapping area 31, which is represented with broad hatching, both with the previous image region as well as with a second overlapping area 32, with the image region being arranged before the previous image region, wherein the second overlapping areas 32 is represented by narrower hatching. This means that each image region is initially registered with the previous image region, as indicated by a first arrow 33, and subsequently additionally registered with the image region that is arranged before the previous image region, which is indicated by the second arrow 34. In this manner, the registration is improved when the individual images 4 are combined into an overall image of the reference object 3.

Figure 4:
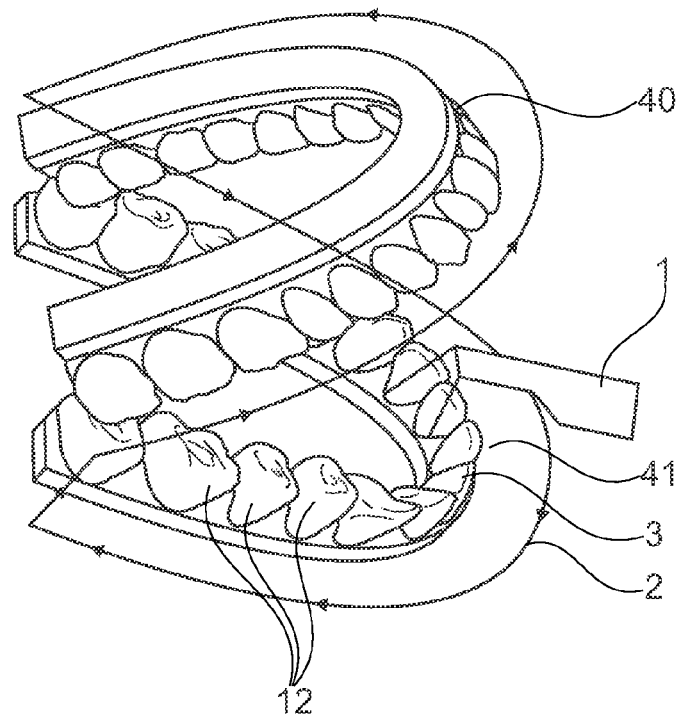
FIG. 4 shows a drawing to clarify an alternative to the present method with a conventional articulator.

FIG. 4 shows a drawing to clarify an alternative to the present method, in which a conventional articulator with a maxilla model 40 and a mandible model 41 is used as a reference model 3, in comparison to FIG. 1 in which a circular reference object is used. The measurement takes place by means of the dental camera 1 along a trajectory 2 that proceeds around the entire articulator and ends back at the starting point. The articulator 3 is measured image-by-image, along the entire trajectory 2, as shown in FIG. 1. Subsequently, the images are registered and an overall image is generated, in which the object regions of the reference object measured twice are used for the comparison in order to determine the measuring error, as explained above with reference to FIG. 1.

Figure 5:
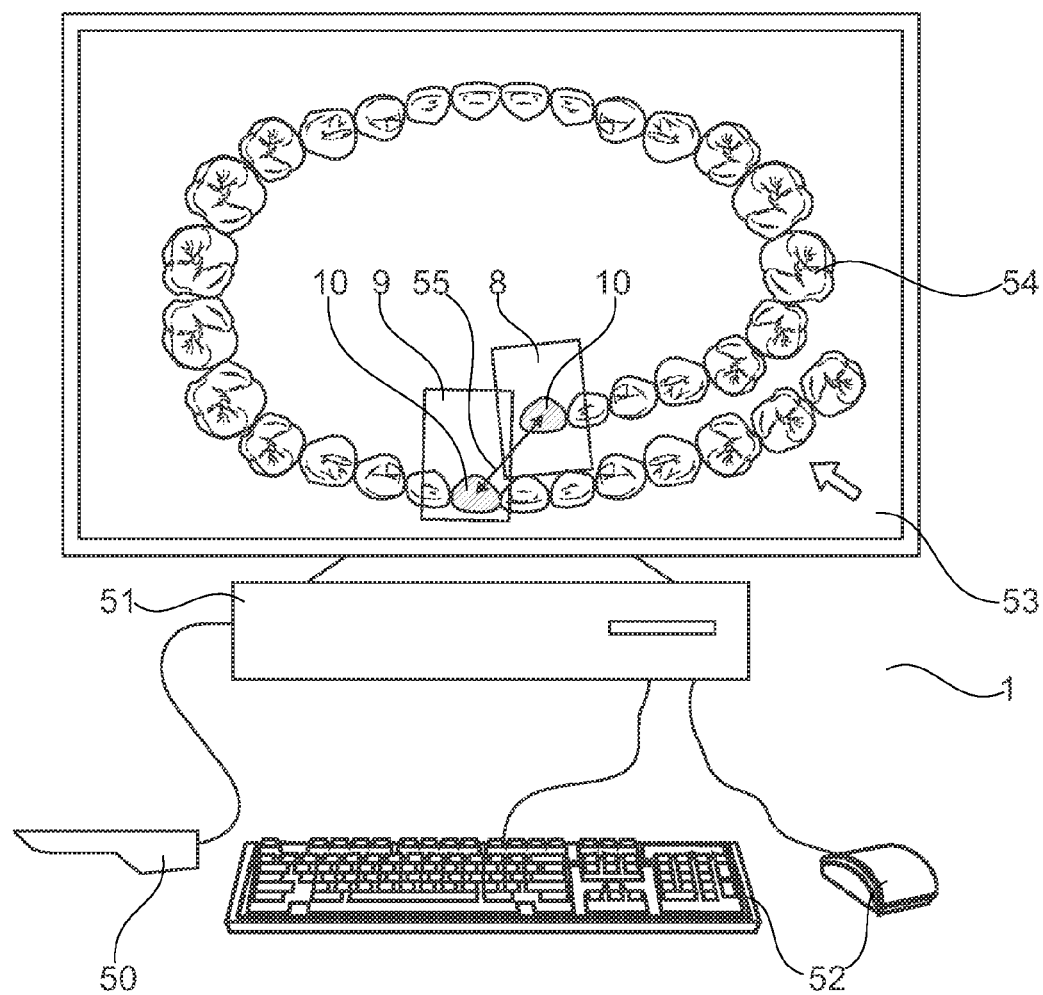
FIG. 5 shows a drawing of the entire measuring system.

In order to explain the present method, FIG. 5 shows the entire measuring system 1 in detail comprising a handpiece 50, which takes the individual images 4 in FIG. 1 while it is being moved relative to the reference object. The measuring system further comprises an image analysis unit 51 such as a computer to which control elements 52 such as a keyboard and a mouse are connected, as well as a display unit 53 such as a monitor. The image data with respect to the images 4 are transferred from the handpiece 50 to the image analysis unit 51 and registered there image-by-image such that the overall image 54 of the reference object 3 from FIG. 1 is generated. In the event of a faulty registration or a faulty calibration, the shape of the images 4 from FIG. 1 will deviate from the actual shape of the reference object 3. The deviation will continue from image to image in the registration, which means that a first position of a twice-measured object region 10 has a distance 55 in the first image region 8 at the start of the measurement and with respect to the position of the object region 10 in the second image region 9 after one circuit. Using the distance 55, the measuring error, which comprises a registration error and a calibration error, of the measuring system 1 can then be determined. If the distance 55 is small enough and within the specified tolerance limits, the tested measuring system will meet the quality requirements. If the distance 55 exceeds these tolerance limits, a subsequent calibration or improvement in the registration algorithm will be required.

REFERENCE NUMBERS

1 Dental camera/measuring system
2 Trajectory
3 Reference object
4 Images
5 Image direction
6 Image regions
7 Overlapping regions
8 First image region
9 Last image region
10 Common object region
11 Arrows
12 Teeth
20 First image direction
21 Tooth axis
22 Second image direction
31 First overlapping region
32 Second overlapping region
33 First registration
34 Second registration
40 Maxilla model
41 Mandible model
50 Handpiece
51 Image analysis unit
52 Control element
53 Display unit
54 Overall image
55 Distance

The invention claimed is:

1. A method of determining a calibration error in a measuring system, the method comprising:
   recording a plurality of three-dimensional images of a reference object from a plurality of different image directions in a circuit along the reference object using the measuring system, wherein an object region of the reference object is imaged twice, at a start of the circuit and at an end of the circuit;
   registering each of the three-dimensional images with another of the three-dimensional images using a registration algorithm for the measuring system so that the three-dimensional images are combined into an overall image;
   determining a distance in the overall image between a first position of the object region in a three-dimensional image from the start of the circuit and a second position of the object region in a three-dimensional image from the end of the circuit;
   determining a total measuring error based on the distance in the overall image;
   determining a registration error of the measuring system from a deviation between an ideal virtual three-dimensional model of the reference object and another virtual model of the reference object generated by applying the registration algorithm for the measuring system to a plurality of virtual sub-regions of the ideal virtual three-dimensional model of the reference object; and
   determining a calibration error by subtracting the registration error from the total measuring error.

2. The method according to claim 1, wherein the reference object is ring-shaped and provides models of multiple teeth next to one another in a row.

3. The method according to claim 2, wherein the measuring system orbits around the ring-shaped reference object during the recording of the three-dimensional images.

4. The method according to claim 1, wherein the reference object is an articulator with a closed upper jaw and lower jaw.

5. The method according to claim 4, wherein a trajectory of the measuring system is along a shape of the articulator during the recording of the three-dimensional images.

6. The method according to claim 1, wherein an image direction of the three-dimensional image from the end of the circuit corresponds to an image direction of the three-dimensional image from the start of the circuit.

7. The method according to claim 1, wherein a first image region of the three-dimensional image from the start of the circuit corresponds, at least partially, to an image region of a following three-dimensional image in the circuit.

8. The method according to claim 1, wherein dimensions of the plurality of virtual sub-regions correspond to dimensions of image regions of the three-dimensional images.

9. The method according to claim 1,
wherein each three-dimensional image partially overlaps with a preceding three-dimensional image in a circuit direction, and
wherein the method further comprises:
registering each three-dimensional image with the preceding three-dimensional image and with a second preceding three-dimensional image that precedes the preceding three-dimensional image in the circuit direction.

10. A dental measuring system, comprising:
a dental camera configured to record a plurality of three-dimensional images from a plurality of different image directions in a circuit along a reference object, wherein an object region of the reference object is imaged twice, at a start of the circuit and at an end of the circuit; and
a computer configured to:
receive the three-dimensional images;
register each of the three-dimensional images with another of the three-dimensional images using a registration algorithm for the dental measuring system so that the three-dimensional images are combined into an overall image;
determine a distance in the overall image between a first position of the object region in a three-dimensional image from the start of the circuit and a second position of the object region in a three-dimensional image from the end of the circuit;
determine a total measuring error based on the distance in the overall image;
determine a registration error of the dental measuring system from a deviation between an ideal virtual three-dimensional model of the reference object and another virtual model of the reference object generated by applying the registration algorithm for the dental measuring system to a plurality of virtual sub-regions of the ideal virtual three-dimensional model of the reference object; and
determine a calibration error by subtracting the registration error from the total measuring error.

11. The dental measuring system according to claim 10, wherein an image direction of the three-dimensional image from the end of the circuit corresponds to an image direction of the three-dimensional image from the start of the circuit.

12. The dental measuring system according to claim 10, wherein a first image region of the three-dimensional image from the start of the circuit corresponds, at least partially, to an image region of a following three-dimensional image in the circuit.

13. The dental measuring system according to claim 10, wherein dimensions of the plurality of virtual sub-regions correspond to dimensions of image regions of the three-dimensional images.

14. The dental measuring system according to claim 10,
wherein each three-dimensional image partially overlaps with a preceding three-dimensional image in a circuit direction, and
wherein the computer is further configured to:
register each three-dimensional image with the preceding three-dimensional image and with a second preceding three-dimensional image that precedes the preceding three-dimensional image in the circuit direction.

* * * * *